United States Patent [19]

Stewart

[11] Patent Number: 4,877,747
[45] Date of Patent: Oct. 31, 1989

[54] OPTICAL ASSAY: METHOD AND APPARATUS

[75] Inventor: William J. Stewart, Blakesley, Northants, England

[73] Assignee: Plessey Overseas Limited, Ilford, United Kingdom

[21] Appl. No.: 848,679

[22] Filed: Apr. 4, 1986

[30] Foreign Application Priority Data

Apr. 12, 1985 [GB] United Kingdom ............... 8509492

[51] Int. Cl.$^4$ .................... G01N 21/77; G01N 33/553
[52] U.S. Cl. ................................. 436/525; 350/96.15;
350/96.19; 350/96.34; 422/57; 422/58; 422/68;
422/69; 435/808; 436/164; 436/805; 436/807
[58] Field of Search ............... 436/164, 525, 805, 807;
422/55, 57, 58, 68, 69; 350/96.12, 96.15, 96.17,
96.19, 96.34; 435/287, 291, 808

[56] References Cited

U.S. PATENT DOCUMENTS

| | | | |
|---|---|---|---|
| 3,853,467 | 12/1974 | Giaever | 436/805 X |
| 3,926,564 | 12/1975 | Giaever | 436/805 X |
| 3,979,184 | 9/1976 | Giaever | 436/525 X |
| 4,222,743 | 9/1980 | Wang | 436/525 |
| 4,521,522 | 6/1985 | Lundstrom et al. | 436/525 |

FOREIGN PATENT DOCUMENTS 1545991 5/1979 United Kingdom .

OTHER PUBLICATIONS

Sutherland, R. M. et al., "Detection of Antibody-Antigen Reactions at a Glass-Liquid Interface as a Novel Optical Immunoassay Concept", Proceedings of 2nd Optical Fibre Conference, (Stuttgart 1984), p. 75.

Primary Examiner—Robert J. Hill, Jr.
Attorney, Agent, or Firm—Fleit, Jacobson, Cohn, Price, Holman & Stern

[57] ABSTRACT

An optical assay apparatus of the type comprising an optic waveguide and a coating sensitized to a specific assay species. The light signal response of the apparatus is enhanced by coupling a resonant metallic medium to the waveguide and to the sensitized coating. To this end, a metal coated transparent buffer layer may be interposed between the waveguide and the sensitized coating. Alternatively, a metallized optically matched grating can be used in place of the buffer layer or the metallic medium can be of particulate form, with each particle having a sensitized coating.

In using the optical assay apparatus, the sensitized coating is exposed to a fluid assay sample. A light beam is directed onto the sensitized coating and reflected onto a detector. The detected light is monitored for any change indicating the presence of the specific assay species in the fluid sample.

12 Claims, 2 Drawing Sheets

OPTICAL ASSAY: METHOD AND APPARATUS

TECHNICAL FIELD

The present invention concerns optical assays and relates in particular to a method and apparatus for detecting and/or monitoring or quantifying the presence and/or behavior of specific molecular species in test fluid samples. The invention is applicable to the following: immunoassays, i.e. the detection of antibodies, antigens, or hormones in blood samples; pollution monitoring; and monitoring of clinical diagnostic reactions involving, e.g., enzymes and the like.

BACKGROUND ART

Immunoassay techniques in the past have often required a complete schedule of analytical steps for species separation and identification. More recently, however, techniques have been developed to obviate the need for bulk separation. These latter techniques rely on "in-situ" separation at the surface of a sensitized detector. Thus, for example, it is already known to detect the presence of antigens in blood samples by causing these antigens to be attracted into an adsorbing layer of a substance containing the appropriate antibody species, with this layer lying adjacent to the gate of an insulated-gate fieldeffect transistor (IGFET)—a so called Chem-FET. The current flow between the source and the drain of this transistor is modified in the presence of antigens in a test sample to which the gate layer is exposed. The transistor current is thus continuously monitored to detect the presence of antigens. After the test, the transistor is disposed of.

There are however, limitations in the response of such Chem-FET devices, and the high cost of such disposable devices mitigates against widespread adoption.

More recently, sensitive, and possibly lower cost, optical assay techniques have been proposed. See for example:—Proceedings of 2nd Optical Fibre Conference (Stuttgart 1984) page 75; "Detection of Antibody—Antigen Reactions at a Glass-Liquid Interface as a Novel Optical Immunoassay Concept", R.M. Sutherland, et al, of the Biomedical Group, Battelle, Geneva, Switzerland (1984). In accordance with the technique that they described, the complimentary antibody is covalently immobilized onto the surface of a planar or fibre optical waveguide. The reaction of immobilized antibody with antigen in sample solution is detected using the evanescent was component of a light beam which has been totally internally reflected many times within the waveguide. This evanescent wave has a characteristic penetration depth of a fraction of a wavelength into the aqueous phase, thus optically interacting with substances bound to or very close to the interface and only minimally with the bulk solution. The efficiency of this technique thus depends on tight confinement of the evanescent wave relative to the interface and this in turn requires a large differential in the value of refractive index on each side of the interface.

DISCLOSURE OF THE INVENTION

The present invention, intended as an alternative to that described above, is aimed at tight confinement of interactive power relative to the sensitized layer, but without necessary resort to a coupling medium of such high refractive index as aforesaid.

In accordance with this invention, there is provided an optical assay method comprising the following steps:

providing a coated metallic medium, the coating thereof being sensitized for a specific assay species; generating in the metallic medium a resonant signal at optical frequency, the power of this signal extending into the sensitized coating;

providing coupling between said resonant signal and a monitored optical beam; exposing the coated metallic medium to a fluid assay sample; and, measuring and changes in the optical beam to detect a response to the presence of the specific assay species in the fluid sample.

In the aforesaid method, tight confinement is achieved at the interface between the metallic medium and the coating. This medium may be, for example, a continuous metal film, and the resonant signal a surface plasmon wave. Alternatively, the metallic medium may be in the form of a dispersion of fine metal particles or a finely divided broken metal film, the resonant signal in this later case resulting from Mie resonance. In both cases the resonance signal power is confined close to the surface of the metallic medium. It is therefore highly sensitive to the structure immediately adjacent to the surface and its sensitivity to, and penetration into, the bulk sample is effectively reduced.

In accordance with one aspect of this invention, there is provided an optical assay apparatus comprising:

a light source;

a light detector;

a propagating medium arranged relative to the source and detector for directing light from the source onto the detector;

a buffer medium of optically less dense material adjacent to a surface of the propagating medium;

a metallic medium, having the form of a continuous metal film, on the surface of the buffer means remote from the propagating medium; and, a coating, adjacent to the metallic medium, sensitized for a specific assay species.

In the above apparatus a plasmon surface wave is generated in the metallic medium by frustrated total internal reflection of the light beam incident from the source. As an alternative to this method of wave coupling and generation, and in place of the buffer medium, the surface of the propagating medium may have the form of a grating of appropriate pitch with the metal film being formed directly thereon.

In accordance with an alternative aspect of this invention, there is provided an optical assay apparatus comprising:

a light source;

a light detector;

a propagating medium, arranged relative to the source and the detector, for directing light from the source onto the detector; and, a dispersion of fine metal particles, each being in contact with a material sensitized for a specific assay species.

In this latter apparatus the resonance in the fine metal particles (Mie resonance) involves a current pattern in each particle with a slightly confined associated external field.

The particles may be distributed in a solution (e.g. as a colloid) or may be confined to the surface of the propagating medium as a broken metal film. In each case, optical excitation and detection is relatively straight forward, involving simply an appropriate incident optical beam.

DESCRIPTION OF THE PREFERRED EMBODIMENTS

Embodiments of the invention will now be described, by way of example only, with reference to the drawings accompanying this specification.

Figure 1:
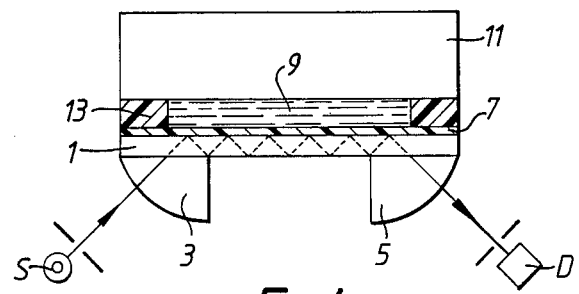
FIG. 1 is a cross-section view of a known optical assay apparatus.

In FIG. 1 there is shown a known form of optical assay assembly in which light from a source S is directed into a planar waveguide 1 by means of a first coupling prism 3 and propagated by multiple total internal reflection to exit by means of a second coupling prism 5 where it is directed onto a light detector D. The external surface of the waveguide 1 is provided with a sensitized organic coating 7. The latter is exposed to a sample liquid 9 which is contained by means of a flow cell 11 and gasket 13 arrangement. In the coating 7, antibody material is covalently immobilized and this responds to any specific antigen material in the sample liquid to which it is exposed. The waveguide is of fused quartz material and this provides a large differential in optical density between the quartz waveguide 1 (high refractive index $n_1$) and the adjacent coating 7 (low refractive index $n_2$). Light is totally internally reflected within the body of the waveguide 1, with a portion of the optical power propagating as an evanescent wave in the coating medium 7. The binding of antigen by the immobilized antibody is monitored by a resultant increase in the light absorption measured at the detector D.

Figure 2:
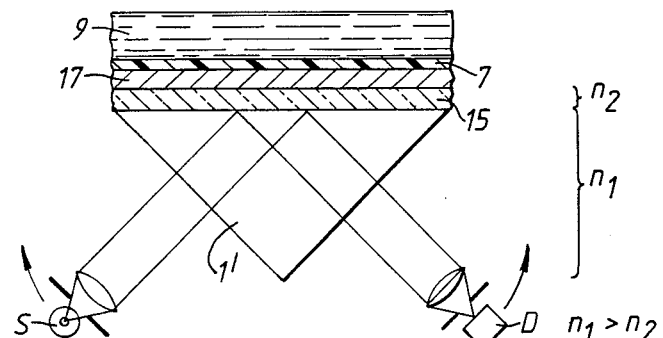
FIGS. 2 to 4 are cross-section views of alternative optical assay apparatus, each embodying the features of this invention.
Figure 5:
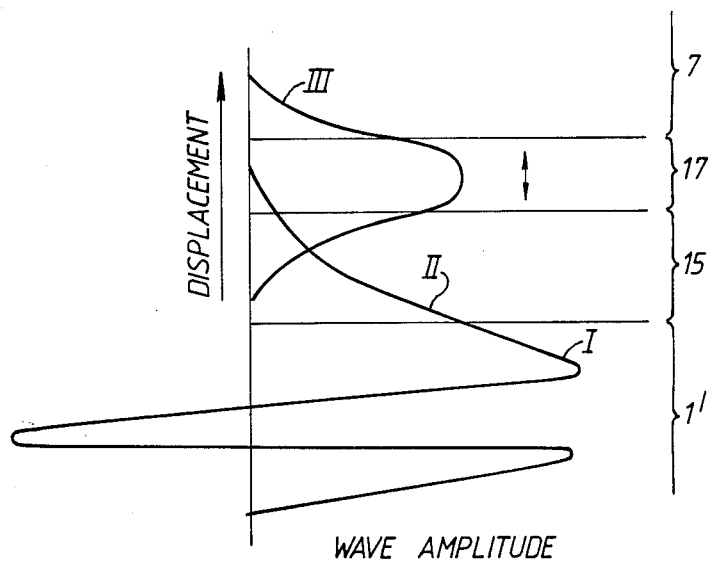
FIG. 5 is a schematic diagram to illustrate attenuation profiles for surface plasmon wave and evanescent optical wave for the apparatus of FIG. 2 preceding.

In the apparatus shown FIG. 2, light of an appropriate frequency is directed from a source S onto a photodetector D via a propagating medium 1'—a prism (as shown) or an optical waveguide. The reflecting surface of this propagating medium 1' is covered by a thin spacer layer, a buffer medium 15 of optically less dense material, and this layer carries a thin layer metallic medium, a continuous metal film 17. This metal film 17 is coated with an organic layer 7, a layer sensitized for the specific assay species for which the apparatus is designed. The organic layer may comprise for example, an antigen for a specific antibody. In use, the organic layer is exposed to a sample fluid 9. In operation, a surface plasmon is generated and sustained in the metallic medium 17. The power for this is supplied by frustrated total internal reflection of the light beam. The wave amplitude profiles for the light beam I, II and for the plasmon wave III are shown in FIG. 5 as a function of displacement. In this figure, regions are delineated for the coating layer 7, the metallic medium 17, the buffer medium 15 and the propagating medium 1'. As shown, the light beam I corresponds to an evanescent wave II in the buffer medium 15. Coupling is provided between the latter and the plasmon wave III. The plasmon wave is tightly confined near to the surfaces of the metallic medium 17, as can be seen from the tail portions of the profile III of the plasmon wave. The thickness of the buffer medium is determined as an optimal solution. If too thick, the coupling is inordinately weak. If too thin, power losses are excessive. The metal film thickness is also chosen as optimal. If too thick the coupling is likewise too weak, and if too thin the plasmon energy is not confined as tightly as desired for this application.

Typical materials and layer thickness are given below:

Organic layer 7~100 Å thick;

Metal film 17 100–400 Å dependant on metal chosen;

Buffer layer 15—Low refractive index, low optical absorptive material—eg. evaporated magnesium fluoride;

Propagating medium—of relatively high refractive index—e.g. flint glass (n=2).

Figure 3:
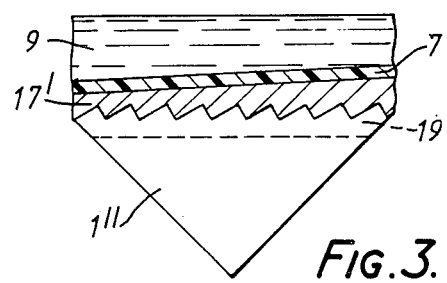

Alternative coupling may be employed, using for example an optical grating. In the alternative apparatus shown in FIG. 3, the reflecting surface of a prism 1" is formed as a grating 19 and a metal film 17' is deposited directly onto the surface of this grating 19. The grating 19 may be defined in the material of the prism 1", or for convenience of construction, may be provided as a bonded component. The pitch $\Lambda_1$, of the grating is chosen to provide a match between the plasmon wave of wavelength $\Lambda_2$ and a light beam of appropriate wavelength $\Lambda_3$. The wavelength—pitch relationship for ideal matching is given as:

$$\frac{1}{\Lambda_3} = \frac{1}{\Lambda_2} \pm \frac{1}{\Lambda_1}$$

Figure 4:
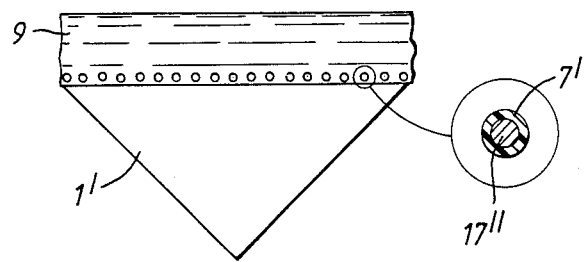

Referring now to the apparatus shown in FIG. 4, the metallic medium is provided as a colloid of fine metal particles 17", each of which has a sensitized organic coating 7'. These particles are arranged so that they settle upon the reflecting surface of the propagating medium, prism 1'.

The presence of assay species may be detected and/or monitored by measuring changes in the absorption or polarization of the monitored light beam. The interaction will depend on the frequency and angle of incidence of the light beam. Thus source S and detector D may be singular components mechanically scanned over a range of angles, or may each comprise an extended array each component being electrically addressed to simulate a scan. Alternatively, the source S and detector D may be set up in an optical static configuration. In certain applications, Raman scattering phenomena may be exploited, and assay species detected by monitoring frequency shift.

What we claim is:

1. An optical assay method comprising the following steps:

providing a coated metallic medium, the coating thereof being sensitized for a specific assay species;

generating in the metallic medium a resonant signal at optical frequency, the power of this signal extending into the sensitized coating;

providing coupling between said resonant signal and a monitored optical beam; exposing the coated metallic medium to a fluid assay sample; and, measuring any changes in the optical beam to detect a response to the presence of the specific assay species in the fluid sample.

2. An optical assay apparatus comprising:

a light source;

a light detector;

a propagating medium arranged relative to the source and detector for directing light from the source onto the detector;

a buffer means of optically less dense material than that of the propagating medium adjacent to a surface of the propagating medium;

a metallic medium, having the form of a metal film, on the surface of the buffer medium remote from the propagating medium; and a coating, adjacent to the metallic medium, sensitized for a specific assay species.

3. An optical assay apparatus comprising:
a light source;
a light detector;
a propagating medium arranged relative to the source and detector for directing light from the source onto the detector;
an optical grating at a surface of the propagating medium;
a metallic medium, having the form of a metal film, on a surface of the optical grating; and
a coating, adjacent to the metallic medium, sensitized for a specific assay species.

4. An optical assay apparatus comprising:
a light source;
a light detector;
a propagating medium, arranged relative to the source and the detector, for directing light from the source onto the detector;
a dispersion of fine metal particles, each coated with a material sensitized for a specific assay species; and
said propagating medium and dispersion of fine metal particles being positioned relative to one another to provide optical coupling therebetween.

5. An optical assay apparatus comprising:
a light source;
a light detector;
a light propagating medium having a reflecting surface, said reflecting surface being arranged relative to the source and the detector for directing light from the source onto the detector;
a coated metallic medium arranged in close proximity to said reflecting surface, said metallic medium having a coating sensitized for a specific assay species; and
said propagating medium and metallic medium being positioned relative to one another to provide optical coupling therebetween.

6. Apparatus as claimed in claim 5, wherein the reflecting surface has the form of an optical grating, and the metallic medium has the form of a metal film on a surface of said optical grating.

7. An optical assay apparatus comprising:
a light source;
a light detector;
a light propagating medium having a reflecting surface, said reflecting surface being arranged relative to the source and the detector for directing light from the source onto the detector;

a coating metallic medium arranged in close proximity to said reflecting surface, said metallic medium having a coating sensitized for a specific assay species; and said coated metallic medium having the form of a continuous thin metal film spaced from the reflecting surface of the light propagating medium by a buffer layer of material optically less dense than that of the light propagating medium.

8. An optical assay apparatus comprising:
a light source;
a light detector;
a light propagating medium having a reflecting surface, said reflecting surface being arranged relative to the source and the detector for directing light from the source onto the detector; and
a coating metallic medium arranged in close proximity to said reflecting surface, said metallic medium having a coating sensitized for a specific assay species; and
said metallic medium having the form of a dispersion of metal particles, with a multiplicity of the metal particles lying upon the reflecting surface.

9. An optical assay method comprising the following steps:
providing a light propagating medium having a reflecting surface, said reflecting surface arranged to direct light from a source onto a detector;
providing a coated metallic medium arranged in close proximity to said reflecting surface, said coated metallic medium having a coating sensitized for a specific assay species;
providing optical coupling between the coated metallic medium and the directed light to generate in the coated metallic medium a resonant signal at optical frequency with the power of said signal extending into the coating;
exposing the coated metallic medium to a fluid assay sample; and
measuring any changes in the directed light to detect a response to the presence of the specific assay species in the fluid assay sample.

10. An optical assay method as claimed in claim 9 further comprising the step of providing a buffer medium of optically less dense material than said propagating medium between said propagating medium and said coated metallic medium.

11. An optical assay method as claimed in claim 9 further comprising the step of providing an optical grating as said reflecting surface.

12. An optical assay method as claimed in claim 9 further comprising the step of laying a multiplicity of metal particles upon the reflecting surface as said coated metallic medium.

* * * * *